United States Patent [19]

Bowers-Irons et al.

[11] Patent Number: 5,085,999
[45] Date of Patent: Feb. 4, 1992

[54] METHOD, APPARATUS, AND REACTANT FOR REMOVAL OF PAINT AND EPOXIES FROM METALLIC BEVERAGE CONTAINERS USING MICROORGANISMS

[75] Inventors: Gail L. A. Bowers-Irons; Quynh K. Tran; Robert J. Pryor, all of Salt Lake City, Utah

[73] Assignee: Technical Research, Inc., Salt Lake City, Utah

[21] Appl. No.: 401,070

[22] Filed: Aug. 31, 1989

[51] Int. Cl.$^5$ .................................. B08B 7/00
[52] U.S. Cl. .......................... 435/264; 134/38; 435/262
[58] Field of Search ............ 435/262, 264; 134/38

[56] References Cited

PUBLICATIONS

He et al., —Chem. Abst. vol. 107 (1987) p. 43719m.
Fujimora et al.—Chem. Abst. vol. 106 (1987) p. 6576w.
Articles from The Proceedings of the Fourth International Biodeterioration Symposium–Berlin, Biodeterioration, edited by Oxley, Becker & Allsopp (Pitman Publishing Ltd., London & The Biodeterioration Society, 1980).
Kestelman, et al., "A Comprehensive Investigation of the Corrosion of Polymeric Materials Used in the Microbiological Fermentation Industry", pp. 61-5.
Osmon, et al., "Rate-Limiting Factors in Biodeterioration of Plastics", pp. 66-75.
Pankhurst, et al., "The Ability of Polymers or Materials Containing Polymers to Provide a Source of Carbon for Selected Microorganisms", pp. 76-90.
Griffin & Turner, "Macrobiodegradation of Plastics", pp. 117-122. Klausmeier, "Mix or Pure Culture Inocula for Assessing Biodeterioration of Plastics: An Interlaboratory Study", pp. 201-07.
Sharp & Woodrow, "A Rapid Test for Biodegradability by Pseudomonas Organisms", pp. 233-37.
Smith & Goulding, "Primary and Secondary Evaluation of Microbiocides", pp. 238-45.
Singh, et al., "Anti-Cockroach and Anti-fungal Surface Coatings", pp. 301-10.
Skinner, "Laboratory Test Methods for Biocidal Paints", pp. 346-54.
Pauli, "Paint Fungicides-A Review", pp. 355-59.
Coleman & Hall, "Some Side Effects of Fungicides in Paints", pp. 360-69.

(List continued on next page.)

Primary Examiner—Sam Rosen
Attorney, Agent, or Firm—Trask, Britt & Rossa

[57] ABSTRACT

A method of removing coatings, such as paint, epoxy resin, comestible polymeric coatings, from the surface of metallic containers, such as aluminum beverage cans, is disclosed. The metallic surfaces of containers are contacted with a mixture of bacteria and nutrient medium. The bacteria used are capable of removing paint, epoxy resins, and coatings from metallic surfaces, and are preferably ATCC #53922 bacteria. Also disclosed is an apparatus suitable for use in the invention, and further described is a reagent for paint removal from beverage cans.

16 Claims, 2 Drawing Sheets

PUBLICATIONS

Hoffmann, "The Development of Fungus-Resistant Paints", pp. 370-75.

Jones & Irvine, "The Role of Marine Fungi in the Biodeterioration of Materials", pp. 422-31.

Lorenz, "Organic derivatives of Tin and Lead in Antifouling Paints", pp. 443-48.

DeWolf, "Some New Considerations on the Testing of Antifouling Paints", pp. 449-55.

Huang, "Biodegradation of Polyurethanes Derived from Polycaprolactonediols", Urethane Chemistry & Application, Holt, Apr. 1981, pp. 471-87.

Zable, et al., "An Accelerated Laboratory Procedure for Growing *Aureobasidium Pullulans* on Fresh Latex Paint Films", vol. 53, No. 675 (Apr. 1981) pp. 33-37.

Horvath, et al., "Paint Deterioration as a Result of the growth of *Aureobasium Pullulans* on Wood", Applied and Envir. Micobiology, vol. 32 (1976) pp. 505-07.

Reynolds, "Pullularia as a Cause of Deterioration of Paint and Plastic Surfaces in South Florida", Mycologia, vol. 42 (1950), pp. 432-48.

Snyder, et al., "New Developments In the Diagnosis of Paint Mildew", Official Digest (Mar. 1952), pp. 149-47.

Barry, et al., "A Method for Testing the Mould Resistance of Paints", *Int. Biodeterior. Bull.*, (159N0020-6164) 13(2) 1977 pp. 51-57.

Cook, et al., "Scanning Electron Microscopic Visualization of Biodegradation of Polycaprolactones by Fungi", *Jr. of Polymer Sci.: Polymer Letters Ed.*, vol. 19 (1981), pp. 159-65.

Evans, et al., "Biodeterioration of Polyester-Based Polyurethane", *Int. Boodetn Bull.*, vol. 4 (2) (1968), pp. 89-92.

Darby, et al., "Fungal Susceptibility of Polyurethanes", *Jr. Applied Microbiol.* vol. 16 (1968), pp. 900-05.

Kaplan, et al., "Microbial Deterioration of Polyurethane Systems", Developments in Industrial Microbiology, vol. 9 (1968), pp. 201-17.

Pathirana, et al., "Gliocladium Roseum (Bainer), A Potential Biodeteriogen of *Polyester Polyurethan Elastomers*", Biodeterioration 5, (1983), pp. 679-89.

Rose, "Microbial Biodeterioration", *Economic Microbiology* vol. 6 (1981), pp. 441-47.

Jones et al., "The Biodeterioration of Polyurethane by Marine Fungi", *Int. Biodetn Bull.*, vol. 6 (3) (1970), pp. 119-24.

Huang, et al., "Biodegradable Polymers: Chymotrypsin Degradation of a Low Molecular Weight Poly(ester-Urea) Containing Phenylalanine", *Journal of Applied Polymer Science*, vol. 23 (1979), pp. 429-37.

Grassie, "Energies of Activation for the Thermal Degradation of Polymers", *Polymer Handbook* (Interscience Pub.), London, pp. V-1-11.

Dombrow, "Polyurethanes", *Reinhold Plastics Applications Series* (Reinhold Publishing Corp., New York) (1957), pp. 1-28.

*Modern Plastics Encyclopedia*, (1983-84), pp. 24-26, 42-62, 76-84.

*Enclyclopedia of Science Technology*, (McGraw-Hill Pub.) (1987), pp. 213-18, 412-13, 130-36, 167-68.

*VanNostrand's Scientific Encyclopedia*, (6th Ed.) 1983, pp. 140-47, 291-92, 423-26, 607-09, 772-73, 1662-63, and 2082-84.

METHOD, APPARATUS, AND REACTANT FOR REMOVAL OF PAINT AND EPOXIES FROM METALLIC BEVERAGE CONTAINERS USING MICROORGANISMS

BACKGROUND OF THE INVENTION

1. Field of Invention

This invention relates to the use of biological processes to remove paint and comestible polymeric coatings from metallic surfaces. In particular, this invention is directed to the biological removal of organic coatings, especially paint or epoxy resins from beverage cans.

2. State of the Art

Today, many food products, especially beverages (e.g. beer and soda), are distributed in metallic containers coated with paint, epoxy resin, or comestible polymeric coating on the interior and exterior surfaces. Aluminum is the predominant type of metallic container for such use. Each year billions of aluminum beverage cans are produced. Within the past several years, it has become necessary to recycle these cans in order to preserve the environment and the earth's limited resources.

Every year over 600,000 metric tons of these aluminum cans are recycled. Heretofore, containers have been incinerated to remove the paint or other coating before recycling. Incineration requires a large investment of energy to remove the coatings from the metal. Furthermore, by incinerating the cans for recycling, the painted or epoxied surfaces of the cans have presented significant environmental risks since incineration can cause the release of toxic materials such as dioxin and other harmful substances into the earth's atmosphere.

Besides the polluting effects of incineration, significant amounts of aluminum are lost to the atmosphere during such processing, causing further pollution and wasting some of the aluminum which could otherwise be recycled. The loss of aluminum ultimately results in an increase in mining which is wasteful of the nation's resources.

It would be highly advantageous to have an energy efficient, low cost, and environmentally safe way to remove coatings from the surface of beverage and other types of metallic containers prior to recycling in order to lessen the pollution of our environment.

Biodegradation of paints and polymers, such as polyurethane, polyesters and polyvinyls, by microorganisms has been reported in the literature. The effect of bacteria on polymers has been reported by Klausmeier, et al. in *Economic Microbiology*, Vol. 6, pp. 441–445 (Academic Press 1981) (discussing the effect of *Pseudomonas aeruginosa* and *Cladosoorium resinae* on polyurethanes); Pankhurst, et al. in "Investigations Into the Effects of Micro-organisms On PVC Pressure-Sensitive Adhesive Tape and Its Constituents", "The Proceedings of the Fourth International Biodeterioration Symposium-Berlin", *Biodeterioration* pp.302-16 (Pitman Publishing Ltd., London and The Biodeterioration Society, 1980) (discussing effects of bacteria on PVC product); and Pankhurst, et al. in "The Ability of Polymers Or Materials Containing Polymers To Provide A Source of Carbon For Selected Microorganisms", "The Proceedings of the Fourth International Biodeterioration Symposium-Berlin", *Biodeterioration*, pp.76-90 (Pitman Publishing Ltd., London and The Biodeterioration Society, 1980). Osmon, et al., in "Rate Limiting Factors In Biodeterioration of Plastics" "The Proceedings of the Fourth International Biodeterioration Symposium-Berlin", *Biodeterioration*, pp. 66-75 (Pitman Publishing Ltd., London and the Biodeterioration Society, 1980), suggests a mechanism of bacterial biodegradation of PVC or other plastic polymers, and Sharpe, et al., "A Rapid Test For Biodegradability By Pseudomonas Organisms" "The Proceedings of the Fourth International Biodeterioration Symposium-Berlin", *Biodeterioration*, pp.233-37 (Pitman Publishing Ltd., London and The Biodeterioration Society, 1980) suggests a methodology for determining bacterial biodegradation of PVC film through detection of ammonium ion increase.

Biodegradation of coatings applied to beverage cans has not been previously accomplished. The constituents of the coatings applied to aluminum beverage cans are generally unpublished due to the proprietary nature of the coatings. However, it is known that epoxy resins are a large component of these coatings. Epoxy resins have, to date, been shown to be resistant to microbial degradation, or even inhibitory of microorganismal growth. See, Pankhurst et al. "The Ability of Polymers Or Materials Containing Polymers To Provide A Source of Carbon For Selected Microorganisms", "The Proceedings of the Fourth International Biodeterioration Symposium-Berlin", *Biodeterioration, pp.*76-90 (Pitman Publishing Ltd., London and The Biodeterioration Society, 1980). "Epoxy resins", as used herein, include paints of which a component is epoxy resin.

"Comestible polymeric coatings", as used herein, refers to those substances typically used as coatings on metallic containers in which food or beverage will be placed so that the food or beverage contained in the container does not react with the metal of the container to cause degradation of the food product, adulteration of flavor, and general contamination of the food. Such materials used for coating metallic containers may be either thermoset or thermoplastic, including phenoxide resins, polypropylene, polyacrylamide, nylon, acrylic resins, and especially epoxy resins. A "coated" surface, as used herein, includes a painted surface, and "coatings" include paints an comestible polymeric coatings: "Paints" are coatings having pigmentation.

SUMMARY OF THE INVENTION

The invention involves contacting the coated surfaces of metallic beverage containers with a reagent. The reagent includes bacteria capable of removing coatings, including epoxy resins, from metallic surfaces in admixture with a nutrient medium capable of sustaining the viability of the bacteria and enabling the bacteria to remove the paint or epoxy resin. The surface to be treated is contacted with the mixture of bacteria and nutrient medium for a sufficient amount of time to allow the bacteria to remove the coating from the metallic surfaces.

The nutrient medium may include any component capable of sustaining bacterial viability. A mixture of beef extract and peptone has been found to be particularly suited to this application.

In practicing the invention, any number of means of maintaining contact of the bacteria and coatings may be employed. For example, the reagent of bacteria and nutrient medium may be sprayed onto the coated metallic surfaces. Alternatively, the metallic containers may be placed in a bath of reagent. When placed in a bath, the metallic containers may first be shredded, by means of cutting or comminuting, to facilitate handling of the material and to enhance the reaction.

Typically, mesophilic bacteria are active for the purposes of this invention at temperatures approaching 45° C., and are especially efficacious at about room temperature (20°-25° C.). Reactions typically take place in an alkaline pH range. Reaction time may vary from an hour to five days or more. Reaction time appears to be dependent in part upon the type and color of paint, epoxy resin or coating being removed. The mixture of reagent and metallic surfaces may be agitated to increase the efficiency of the reaction. After the reagent has been in contact with the coated metallic surfaces for some time, the coating begins to "flake off" the surface.

Although not required, further processing may be desired to hasten the removal process, including subjecting the metallic surfaces to a jet spray action, ultrasound, or an abrasive treatment to remove the loosened coating. This processing may be optionally followed by re-treating the metallic surfaces with the reagent for further removal of coating. The removal process may also be hastened by treating the aluminum cans with detergent. After the coating or epoxy resin has been removed, the containers may then be processed for aluminum recovery or recycling.

Following a treatment of metallic containers, the reagent may be clarified by separating from it any dissolved coating or precipitate. The clarified reagent may then be reused in a subsequent treatment. It may be desirable or necessary to add more bacteria and more nutrient medium.

DETAILED DESCRIPTION OF THE PREFERRED EMBODIMENTS

I. Bacteria

Figure 1:
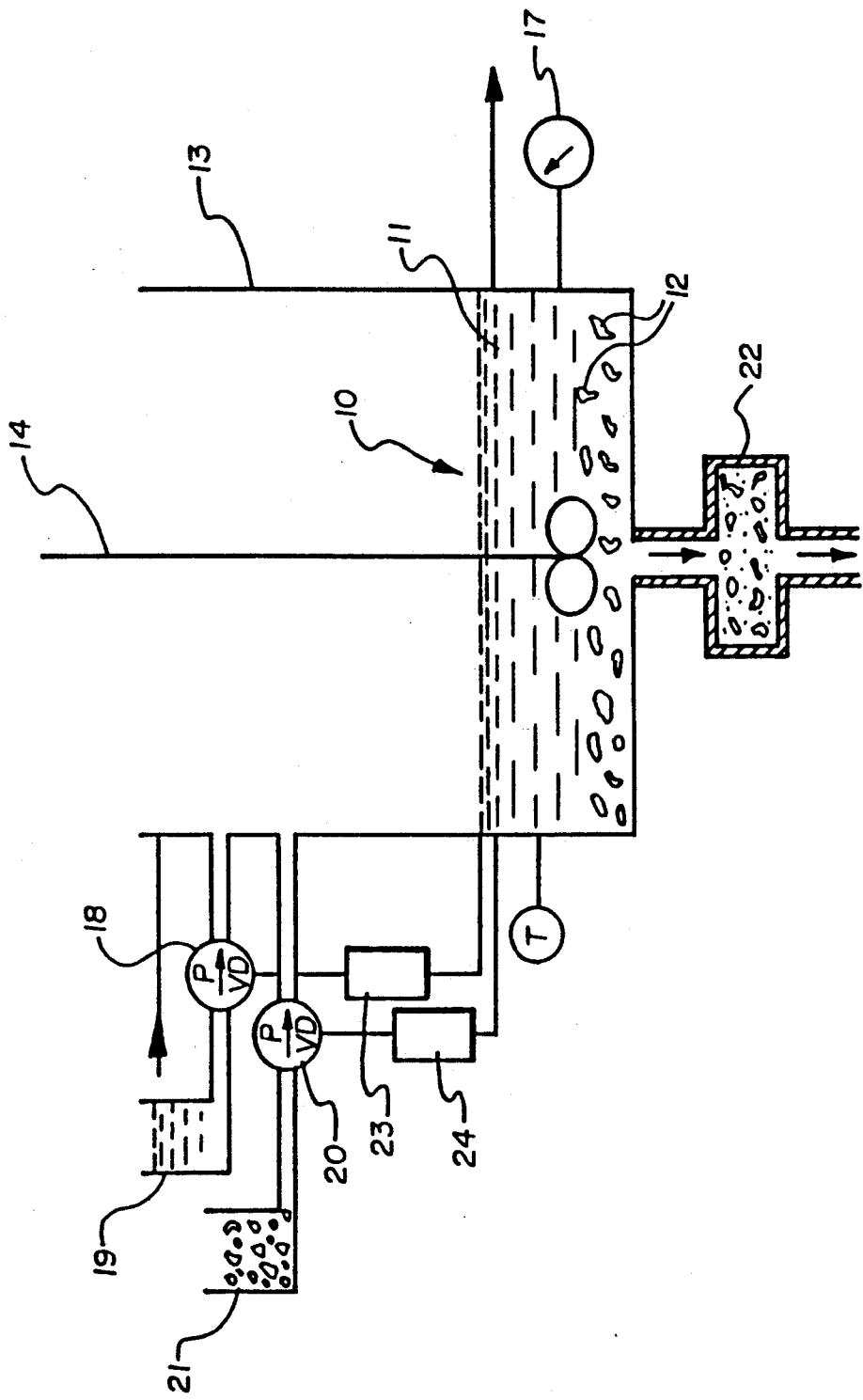
FIG. 1 is an idealized schematic drawing illustrating apparatus useful in the practice of the invention.

Bacteria capable of removing coatings from metallic beverage containers are typically mesophilic, operating at a mid-range of temperatures between 20° centigrade (C) and 45° C. Reactions preferably take place at temperatures between 20° C. and 25° C., however. Mesophilic bacteria occur in nature and are readily discoverable in soils. Soils preferred are those found in metal scrap yards.

Once a source of mesophiles has been identified, various strains of the bacteria can be isolated using well-known techniques. For example, the bacteria may be streaked onto a sterile glass petri dish containing solid or semi-solid nutrient medium. This medium contains nutrients which the bacteria can use as food.

Within a few days, the various bacterial cells should reproduce, covering the medium with colonies of bacteria. Assuming individual cells were well separated in the initial streaking, isolated colonies will have arisen from a single bacterium and will therefore be composed of many identical organisms.

If such a colony is touched with a sterile needle and the adhering cells transferred to another sterilized medium, the bacteria will reproduce as a pure culture (a culture composed of a single type of bacterium).

Other well-known pure culture techniques such as "streak-plate" or "pour-plate" methods may be used to obtain pure bacterium cultures. The bacteria may also be sustained on a liquid medium such as infusion media.

The medium may also contain a coated metal surface. In such a case, the medium can be used as a preliminary screening step to determine if the bacteria are capable of disrupting the adherence of the coating from metallic surfaces. This preliminary screening step will generally not be used with agar media.

Once the bacteria has been isolated into a pure culture the bacteria can be further tested to determine whether or not it can be used to remove the coating from metallic surfaces. One such test technique is to incorporate the isolated bacteria into the processes of the hereinafter described Examples and then analyze the culture medium for the presence of unadhered or dissolved coating.

Preferred bacteria for use in the invention are ATCC #53922 which were deposited with the American Type Culture Collection, 12301 Parklawn Drive, Rockville, Md. 20852, U.S.A., under the Budapest Treaty on June 20, 1989. The American Type Culture Collection is an approved depository which will provide access to the ATCC #53922 bacteria during the pendency of this application and which will irrevocably remove all restrictions on the availability of the ATCC #53922 culture to the public upon the granting of a patent. ATCC #53922 bacteria are a mixed culture of two bacteria species. Both species are capable of removing paint and epoxy resin either separately or in conjunction with one another. One specie is *Pseudomonas picketti*, and the other is an as yet unidentified Bacillus species. The *Pseudomonas picketti* is gram (−) oxidase-positive and catylase-positive. The Bacillus species is gram (+) oxidase- (−) and catylase-positive. ATCC #53922 bacteria are a subculture of a bacterium taken from the soil of an auto junk yard in Salt Lake City, Utah. The bacteria were extracted from soil samples containing paint wastes. Subcultures were subjected to varying concentrations of a variety of paint types thereby producing a subculture of what are believed to be naturally mutated bacteria particularly capable of degrading such coatings.

Mutations of ATCC #53922 bacteria which have occurred naturally or under induced conditions (e.g. growth in the presence of ultra violet light) may also be used when the mutation still displays an affinity for degrading paint or epoxy resin. Recombinant forms of ATCC #53922 bacteria may also be used. Recombinant forms include host cells, such as other prokaryotic cells or eucaryotic cells, into which all or part of the DNA of ATCC #53922 bacteria has been placed such that the host cell organism is then capable of biodegrading paint and epoxy resin.

Techniques for producing mutations, either naturally or artificially, and for producing recombinant forms are known in the art, and are discussed in various publications, such as Watson, et al. *The Molecular Biology of the Gene*, Vol. 1 pp. 3-585 (W. A. Benjamin, Menlo Park, Calif., 4th ed. 1987) (mutations); Beers et al. *Cell Fusion: Gene Transfer and Transformation*. pp. 79-275 (Raven Press 1984); Denniston et al., *Recombinant DNA*, pp. 109-290 (Bowbin, Hutchinson, Strasburg, Pa. 1981); Chafer et al. *Genetic Rearrangement*, pp. 59-74 (Sinauer Assoc. 1980); and Kushev, Mechanisms of Genetic Recombination, pp. 5-175 (Consultants Bureau 1974) the contents of each hereby being incorporated by this reference.

The selected bacteria are added to a nutrient medium to maintain viability of the bacteria. A number of such nutrient media are available, but the hereinafter described mixture of beef extract and peptone is the preferred medium for bacterial viability and enhanced coating removal. See II and III below. The mixture of ATCC #53922 bacteria or its mutant or recombinant forms, and beef extract and peptone produces a unique reagent which is especially adapted to the process described by this invention.

II—Nutrient Media to Maintain

Experiments were performed to determine the efficiency of various nutrient media as a vehicle for maintaining bacterial growth and paint removal advancement. All references to percent are weight to volume percentage ratios.

| A. Beef Extract/Peptone Nutrient Broth | |
| --- | --- |
| Beef Extract | 0.3% |
| Peptone | 0.5% |
| deionized $H_2O$ | QSAD to 10 liters |
| B. Inorganic Nutrient | |
| Ammonium Sulfate - $(NH_4)_2 SO_4$ | 0.3% |
| Ferrous Sulfate - $FeSO_4.7H_2O$ | 0.3% |
| Potassium Chloride - KCL | 0.01% |
| Calcium Nitrate - $Ca(NO_3)_2.4H_2O$ | 0.01% |
| Potassium Dihydrogen Phosphate - $KH_2PO_4$ | 0.05% |
| Magnesium Sulfate Heptahydrate- $MgSO_4.7H_2O$ | 0.05% |
| Water - $H_2O$ | QSAD to 10 liters |
| C. Potato Sucrose | |
| Preparation: Cook 200 grams (g) diced potatoes in 0.5 l distilled water for 10 minutes, filter through cheesecloth and add distilled water to 1.0 l then add 20.0 g sucrose. | |

Experiments were conducted using the three media in admixture with a culture of bacteria taken from the soil of an auto junk yard. A fourth test was run using a thermophilic bacteria denoted as ATCC #53921 in admixture with 9K, a nutrient medium containing ammonium phosphate (0.3%), potassium chloride (0.1%), potassium orthophosphate, mono-H (0.5%) magnesium sulfate heptahydrate (0.5%), and ferrous sulfate heptahydrate (45.0%).

The inorganic nutrient (B., above) was specifically used in order to force the organism to utilize the coating on the cans as a carbon source, but the inorganic nutrient was found to cause corrosion of aluminum.

Each experiment was conducted by adding ten percent to forty percent by weight aluminum cans to the bacteria and nutrient medium admixture. Each admixture of bacteria and nutrient medium contained approximately $3.075 \times 10^8$ colony forming units (CFU)/ml of bacteria in the medium. Each experiment was run at room temperature (20° C. to 25° C.). Each experiment was run for 183 days with little degradation having occurred.

III—Nutrient Media to Enhance Reaction

Another experiment was conducted in which ATCC #53922 bacteria were mixed with the beef extract and peptone nutrient broth. The nutrient broth was prepared by mixing powdered 0.3% beef extract (Difco Labs, Detroit, Mich. or Sigma beef extract #B-4888), and 0.5% peptone (Difco Labs, Detroit, Mich.) with a quantity sufficient of water to make 10 liters of broth. Enough bacteria were added to achieve a $3.075 \times 10^8$ CFU/ml concentration for coating removal. Aluminum cans which had been cut into pieces and autoclaved were then added to the bacteria and beef extract/peptone nutrient medium admixture. After five days the paint was completely removed from the aluminum pieces.

In a preferred embodiment of the invention, an admixture of bacteria and beef extract/peptone nutrient medium is first prepared. The admixture is placed into a container such as a vat or bioreactor. A bioreactor usable in similar applications is that disclosed in U.S. Pat. No. 4,728,082 to Emmett, Jr., et al. the contents of which are incorporated by this reference.

The apparatus illustrated schematically in FIG. 1 presents a preferred system for carrying out the invention. An admixture, generally 10, of nutrient medium 11 and bacteria 12 is placed in a reaction vessel 13. The apparatus has an agitator 14 for agitating the admixture. The agitator may generally be a slurry-type mixer comprising a shaft centered relative to the vessel with radiating arms which rotate so as to mix the contents of the vessel. A thermostat 16 may be used to control the temperature of the reaction, and a pH meter 17 monitors the pH of the admixture. A pump capable of intermittent release 18 controls the addition of nutrient medium 19 when release is indicated by monitor 23. Another intermittent release pump 20 controls the addition of bacteria 21 as determined by monitor 24. After the reaction has taken place and coating removed from the cans has mixed with the admixture, the coating precipitate can be filtered from the admixture via a filtering system 22.

Figure 2:
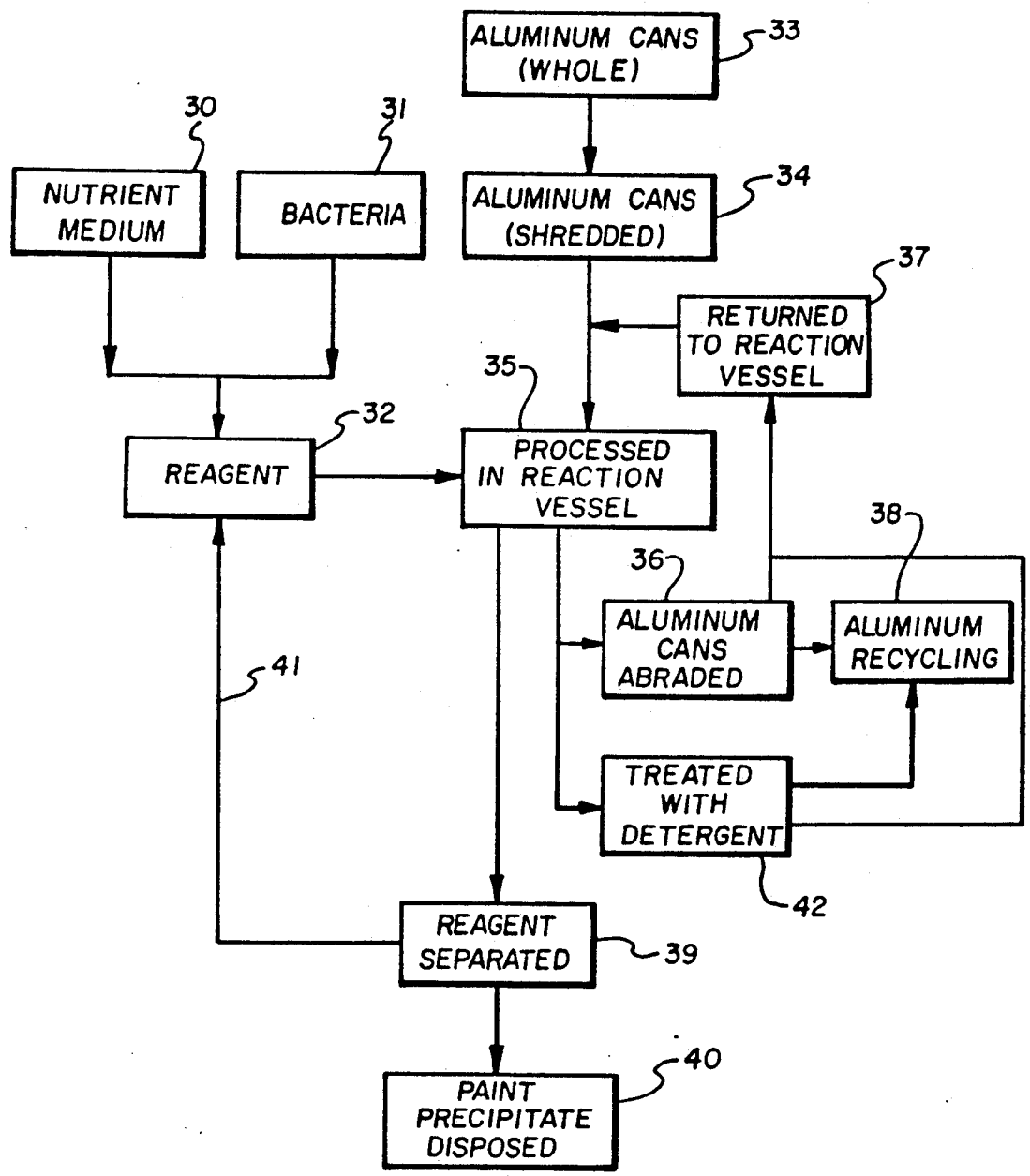
FIG. 2 is a flow diagram illustrating an embodiment of the invention.

FIG. 2 illustrates a method of the invention in greater detail. Nutrient medium 30 and bacteria 31 are admixed to form the reagent 32. Aluminum cans 33, (e.g. discarded Coke ® cans) which may first be shredded 34 to enhance the reaction, but need not be shredded, are placed in the reaction vessel with the reagent 35. Following a time sufficient for the reagent to disrupt the bonding of the coating to the can (e.g. one day), the reacted aluminum cans may optionally be removed from the vessel and optionally subjected to an abrasive treatment 36 to remove any loosened coating. This abrasion procedure hastens the removal of coating. The removal of coating may also be hastened by treating the cans with a detergent 42. If all of the paint or other coating has not been removed following the abrasion procedure or treatment with detergent, the cans may then be returned 37 to the reactor for reprocessing. If all of the paint or coating has been removed, however, the cans can then be further processed or recycled 38 for aluminum. The abrasion step and detergent treatment are optional and may not be necessary at all. The reagent admixture may be filtered or otherwise physically separated 39, i.e. centrifuged, to remove precipitate in the reagent, and the precipitate is disposed 40. The filtered reagent is then returned to the reaction vessel for processing, and new media or bacteria may be added as needed.

The mixture of reagent and containers is maintained at a pH range of about 8.0 to about 9.5. The reaction takes place at about room temperature, or about 20° C. to about 25° C. Within an hour the reagent begins to disrupt the bonding of paint or epoxy resin to the metallic surface. Within twenty-four hours, paint adhesion has been significantly disrupted. Disruption of bonding of paint to the container seems to be variably dependent upon the color of paint being removed. If ATCC

53922 bacteria and beef extract/peptone nutrient are used, most colors of paint are removed within twenty-four hours, while black paint takes considerably longer (five days).

At any stage during the biodegradation procedure, the beverage cans may optionally be removed and further treated by, for example, subjecting to a jet spray action, brushing, abrasion, ultrasound, agitation, or other processes to remove loosened coating. The cans may also be removed from the reagent and treated with a detergent to aid in removal of coating. Removal of the paint or other coating by the reagent may be sufficiently complete so that abrasion or treatment with detergent is unnecessary. Thereafter reprocessing in the reagent may re-commence for further biodegradation.

In the preferred embodiment slight agitation of the reagent and beverage cans during biodegradation enhances the process.

When processing of the metallic surfaces is complete, the precipitate which forms in the admixture is then separated and removed from the admixture. Separation can be accomplished by any method, including filtration and centrifugation. The admixture may then be used again in subsequent processing. Cans from which the paint and epoxy have been removed may then be further processed according to well-known recovery techniques for aluminum (e.g. refining to form raw aluminum).

Additional details of the invention will appear from the Examples in conjunction with the figures and the claims.

EXAMPLES

Example A

Aluminum cans with paint and comestible polymeric coating on the exterior and interior surfaces respectively were prepared by removing the top and bottom portions of the cans, and cutting, with a pair of snips, the remaining can into pieces approximately three centimeters by two centimeters. The pieces were then autoclaved at 15 psi and 121° C. for twenty minutes. Aluminum fragments having an average weight of 254.4 grams (g) were added to five liters (l) of admixture containing beef extract/peptone nutrient broth and ATCC #53922 bacteria in a quantity sufficient to reach critical mass for coating removal. Reaction took place at room temperature (20° C. to 25° C.), and at a pH of 7.5 to 9.5, with an average of 8.6. On the fifth day of reaction, all of the coatings had been removed from the aluminum pieces.

Example B

One aluminum can weighing 6.970 g was added to an admixture of beef extract/peptone nutrient broth and ATCC #53922 bacteria in a bioreactor vat. The can and admixture were reacted at room temperature (20° C. to 25° C.) and at an average pH of 8.6. On day three, an amount of bacteria was removed from the admixture of nutrient broth/bacteria/aluminum can. Gram staining indicated that approximately ninety percent of the bacteria stained negatively; the bacteria appeared to be a mixture of cocci and rods. On day seven, no degradation had taken place. The aluminum can was removed from the admixture and autoclaved at 121° C. for approximately 20 minutes. It was then returned to the bioreactor after having been turned inside out. The pH of the nutrient broth/bacteria admixture measured 8.56. On day nine, gram staining of a bacteria sample from the admixture showed that all bacteria were stained negatively, and a majority of the bacteria were cocci. On day ten, no degradation had taken place although the paint on the can looked lighter in color. Some corrosion was observed on day eighteen. The admixture was filtered to remove all sediment, and the filtered admixture and can were returned to the bioreactor. On day twenty-two, all paint had been removed from the can, and a 0.057 g weight reduction in the can was measured.

Example C

In a bioreactor with aeration capability, 0.5% Tween 80 (Atlas Chemical) in 700 ml of beef extract/peptone nutrient broth was added with 36.255 g of aluminum can pieces which had paint or epoxy resins on the surfaces. ATCC #53922 bacteria were added to achieve a critical mass for biodegradation ($3.075 \times 10^8$ CFU/ml). Two liters of distilled water were added and the bioreactor was engaged. Air was initially infused into the bioreactor. An excessive amount of foam was produced, however, and the air was discontinued.

The initial pH of the beef extract/peptone nutrient broth was 7.0. Following reaction at room temperature (about 20° C. to 25° C.), the pH of the nutrient broth/bacteria/aluminum can admixture was 8.51. On day twenty-two of the experiment, all paint had been removed from the aluminum can pieces. The aluminum can pieces were removed from the nutrient broth/bacteria admixture and were weighed. Small shards of aluminum had been lost in the reaction with a net reduction in weight of 5.269 g.

Example D

Four 250 ml Erlenmeyer flasks were filled with 150 ml each of beef extract/peptone nutrient broth prepared by mixing the powdered forms of beef extract and peptone purchased from Difco Labs (Detroit, Mich.) in a concentration of 0.3% beef extract and 0.5% peptone to a quantity of de-ionized water to make 10 l.

Each flask was inoculated with a bacterial colony taken from one of four plates prepared by standard streaking techniques. Coca-cola ® beverage cans (Classic Coke) were prepared by removing the top and bottom of the can and cutting the remaining cans with tin snips into pieces approximately $3 \times 4$ cm. To flask one was added 0.821 g of Coke can pieces; to flask two was added 0.635 g of Coke can pieces; to flask three was added 0.577 g of can pieces; and to flask four was added 0.627 g of can pieces.

The can pieces were reacted in each of the four flasks at room temperature (20°-25° C.), and at a pH range of 7.0 to 8.6. On day three of the experiment 95% of the paint had been removed from the can pieces in flask one with only white paint remaining, which could be removed by scraping with a fingernail. Approximately 85-90% of the paint on the can pieces in flask two had been removed, and what paint remained could not be scraped off. In flask three, approximately 80% of the paint had been removed, and what paint remained could not be removed. In flask four, about 99% of the paint had been removed, and it was observed that approximately 50% of the white paint on the can remained. No further reaction was undertaken.

Example E

A sample of material was taken from a bioreactor which, following analysis, was shown to contain a fungal contaminant, a darkly colored bacteria, and a lightly colored bacteria, the latter two forms comprising ATCC #53922 bacteria. Each organism was separated and cultured on individual plates using standard streak plate techniques. It was observed that the darkly colored bacteria culture comprised rods of gram negative bacteria. It was further observed that the culture of lightly colored bacteria comprised rods of gram positive bacteria.

Four flasks were prepared by inserting into each 100 ml of beef extract/peptone nutrient broth. Flask one was inoculated with purified fungus by means of an inoculum needle touched to the plate of fungus; flask two was similarly inoculated with purified, darkly colored bacteria; flask three was similarly inoculated with purified, lightly colored bacteria; and flask four was inoculated with 5 ml of the mixture taken from the bioreactor. Each flask was then shaken to disperse the inoculant.

Pieces of a Sprite ® can were prepared by cutting off the top and bottom of the can and cutting the remaining can into pieces approximately 3 cm by 4 cm. A piece of can was added to each of the four flasks. The weight of the can pieces measured 0.178 g, 0.181 g, 0.129 g and 0.171 g, respectively. The contents of the flasks were reacted at room temperature (20°-25° C.) and at a pH of 7.0 to 9.5. After twenty-four hours, the pieces of can were removed from each flask. The piece of can from flask one had lost no weight and no paint had been removed. All of the paint on the piece of can in flask two had been removed. Similarly, the paint had been removed from the piece of can in flask three. Only some of the paint had been removed from the piece of can in flask four, and none of the green paint had been affected at all.

Example F

A six liter culture of beef extract/peptone nutrient broth, prepared as for other experiments, was placed in a 10 l Corning Pyrex jar on a stirplate. The broth was inoculated with ATCC #53922. On day twenty-seven of the experiment, a whole Coke ® can (bottom and top portions not removed) was added to the nutrient broth in the jar. The pH was determined to be 8.20. On day twenty-eight no paint had been removed. The pH of the nutrient broth/bacteria admixture was adjusted to 9.10 by addition of 6 ml of 1N NaOH. Red paint particles were observed floating in the admixture following adjustment of the pH on day twenty-eight. The can was removed on day twenty-nine and treated with Alconox ® (Alconox, Inc., N.Y., N.Y.), a glassware detergent, to remove the remaining paint on the can completely.

On day twenty-nine, the pH of the admixture was measured at 8.56. The pH of the admixture was adjusted to 9.10 by addition of 4 ml of 1N NaOH. One and one-half liters of pH 9.10 nutrient broth were added to the existing admixture. A whole Coke ® can was suspended in the admixture with only one half of the can being in contact with the admixture. The paint on the submerged portion of the can was almost entirely removed in two and one-half hours; treatment with Alconox ® removed any residual paint remaining on the can.

A technique for attaining a pure culture of bacteria capable of removing paint and epoxy resins is illustrated in the following example:

Example G

A soil sample taken at an auto wrecking yard is used to inoculate a medium (e.g. the previously described beef extract/peptone nutrient broth). The medium contains therein shreds of painted aluminum cans and is maintained at room temperature (about 25° C.). Mixed bacterial colonies are allowed to grow in this medium creating a mixed culture. This procedure preliminarily screens the mixed culture of bacteria and other microorganisms not able to survive in an environment containing metallic aluminum, paints and epoxy resins.

The mixed culture is then diluted with sterile water using sterile techniques. The dilution of mixed culture is then immediately used to inoculate a test tube containing a melted agar medium that has been cooled to 25° C. The test tube is then agitated to disperse the organisms throughout the medium before being poured into sterile petri dishes and allowed to solidify. Alternatively, a liquid nutrient broth or agar may be used. A culture derived by this method generally results in evenly dispersed colonies. Such dilutions must contain enough organisms to provide a number of separate colonies on each plate without covering the petri dish with colonies that have grown together which may require several different dilutions to be plated.

Each of the separate colonies is then tested for its ability to disrupt the adherence of the paint from the aluminum surface. Such testing may be done as described in Examples A through F, above, substituting the bacteria being tested for ATCC 53922 bacteria.

Transfer of genetic material between bacteria for the purpose of producing genetic recombinations can be mediated by several means, including generally, conjugation, transduction, or transformation. Detection of plasmids for paint or epoxy resin removal can be undertaken by the methods discussed in *Genetics of Bacteria* by Scaife, et al., Academic Press, London (1985), pp. 165-70. An example of plasmid determination and transformation for genetic recombination is set forth in Example H:

Example H

ATCC #53922, which are capable of removing paint and epoxy resins from aluminum beverage cans, are grown in 250 ml of L-broth. After twenty-four hours, the bacteria are centrifuged for 10 minutes at 6,000 revolutions per minute (rpm) at 4° C., followed by resuspension in 3 ml of ice cold 25% sucrose in 50 mM Tris-HCl. To the suspension is added 0.5 ml of 10 mg/ml lysozyme in 50 mM Tris-HCl. One milliliter of 0.25 M EDTA is added and the mixture is incubated at room temperature for 5 minutes. Two and one-half milliliters of 20% SDS in TE buffer is added, the mixture is agitated manually to complete lysis, and the mixture is then incubated at 55° C. for a few minutes. The DNA is then denatured by adding 0.75 ml of 3M NaOH and gently mixing. Then 6.0 ml of 2M Tris is added and the mixture is shaken gently. Three milliliters of 20% SDS is then added followed by 6 ml of ice cold 5M NaCl. The mixture is allowed to stand for twelve hours at 4° C. The flocculent precipitate is centrifuged at 20,000 rpm for 30 minutes. To that is added one third volume of 42% polyethylene glycol 6,000 and the mixture is shaken gently and incubated overnight at 4° C.

The precipitated DNA is centrifuged at 7,000 rpm for 6 minutes, and is resuspended by addition of 8 ml of TE buffer. The mixture is then banded in a CsCl gradient in the presence of ethidium bromide as discussed in *Basic Cloning Techniques* by Pritchard and Holland, Blackwell Scientific Publications, Oxford (1985), pp. 63-8 the contents of which are incorporated herein.

Extracted plasmid is then treated by the method disclosed in U.S. Pat. No. 4,468,464 (Cohen, et al.), the contents of which are incorporated herein, to produce a plasmid form which can then be transformed by another prokaryotic or eucaryotic microorganism. Transformation generally is accomplished by mixing the prepared plasmid DNA with "competent" cells, for example, *E. coli* bacteria, which have been made competent, or able to transform plasmid DNA. Preparation of competent cells is accomplished by the method described in *Basic Cloning Techniques* by Pritchard and Holland, Blackwell Scientific Publications, Oxford (1985), pp. 36-7. The mixture of plasmid DNA and competent host cells is then heated at 42° C. for a few minutes. The plasmids enter the host cell during that time.

Host cells which have been transformed are then cultured by standard "streak-plate" or "pour-plate" techniques and the resulting cells are tested for the phenotypic characteristic of paint or epoxy removal following the techniques described in the foregoing examples.

Reference to specific embodiments or examples are not intended to limit the scope of the appended claims.

We claim:

1. A method of removing from a metallic surface paint, epoxies and comestible polymeric coatings comprising:
    contacting the coating on a metallic surface with a reagent comprising, in admixture, organisms predetermined to be capable of removing said coating from metallic surfaces and a nutrient medium capable of maintaining said organisms and enabling said organisms to remove said coating, said organisms being selected from the group consisting of bacteria having deposit accession number ATCC 53922, mutated bacteria derived from bacteria having deposit accession number ATCC 53922, host cell organisms containing DNA derived from bacteria having deposit accession number ATCC 53922, and mixtures thereof; and
    maintaining said contact for a time sufficient to disrupt the adhesion of said coating to the metallic surface.

2. The method according to claim 1 wherein the nutrient medium comprises an admixture of beef extract and peptone.

3. The method according to claim 2 wherein said metallic surfaces are aluminum beverage cans.

4. The method according to claim 3 further comprising shredding the aluminum cans before contacting with said reagent.

5. The method according to claim 4 wherein said contact takes place in means for containing said reagent and said metallic surfaces.

6. The method according to claim 5 in which said disruption takes place at about 20° C. to about 25° C.

7. The method according to claim 6 in which said disruption takes place at a pH range from about 7.5 to about 9.5.

8. The method according to claim 7 wherein said contact of the reagent with said coating on said metallic surfaces is maintained for at least twenty-four hours.

9. The method according to claim 8 wherein said reagent and said metallic surfaces are agitated during processing.

10. The method according to claim 9 further comprising separating the unadhered coating from said metallic surfaces after reaction of said coating with said mixture of nutrient medium and organisms.

11. The method according to claim 10 further comprising reprocessing said metallic surfaces by recontacting said metallic surfaces with said reagent.

12. A composition of matter capable of removing paints, epoxies and comestible polymeric coatings from metal surfaces, said composition comprising an admixture of organisms selected from the group consisting of ATCC #53922 bacteria, mutations of ACTT #53922, genetic recombinations of ATCC #53922 bacteria, and prokaryotic and eucaryotic forms containing all or part of the DNA of ATCC #53922 bacteria, and a nutrient medium capable of maintaining said organisms and enabling the organisms to remove said coatings.

13. The composition of matter according to claim 12 in which said nutrient medium comprises a mixture of beef extract and peptone.

14. An apparatus for removing paints, epoxies, and comestible polymeric coatings from metallic beverage containers, said apparatus comprising, in combination: organisms selected from the group consisting of ATCC #53922 bacteria, mutations of ATCC #53922 bacteria, genetic recombinations of ATCC #53922 bacteria, and prokaryotic and eucaryotic forms containing DNA of ATCC #53922 bacteria;
    a nutrient medium capable of maintaining the growth of said organisms and capable of enhancing the removal of paints, epoxies and comestible polymeric coatings from metallic beverage containers; and
    means for containing said organisms, nutrient medium and said metallic beverage containers.

15. The apparatus of claim 14 further comprising means for regulating the temperature of said admixture in reaction with said beverage containers.

16. The apparatus of claim 15 further comprising means for agitating said admixture and said beverage containers.

* * * * *